(12) United States Patent
Maubru

(10) Patent No.: US 6,187,057 B1
(45) Date of Patent: Feb. 13, 2001

(54) DIRECT HAIR DYEING COMPOSITION COMPRISING A CROSS-LINKED POLYMER WITH ACRYLIC AND/OR ACRYLATE UNITS AND WITH ACRYLAMIDE UNITS

(75) Inventor: Mireille Maubru, Chatou (FR)

(73) Assignee: L'Oreal, Paris (FR)

( * ) Notice: Under 35 U.S.C. 154(b), the term of this patent shall be extended for 0 days.

(21) Appl. No.: 09/068,963

(22) PCT Filed: May 20, 1997

(86) PCT No.: PCT/FR97/00884

§ 371 Date: May 20, 1998

§ 102(e) Date: May 20, 1998

(87) PCT Pub. No.: WO97/44003

PCT Pub. Date: Nov. 27, 1997

(30) Foreign Application Priority Data

May 23, 1996 (FR) .................................................. 96 06429

(51) Int. Cl.[7] ...................................................... A61K 7/13
(52) U.S. Cl. ........................... 8/405; 8/414; 8/415; 8/428; 8/558; 8/679
(58) Field of Search ................................ 8/404, 405, 414, 8/415, 425, 426, 428, 558, 679; 424/70.16

(56) References Cited

U.S. PATENT DOCUMENTS

| | | | |
|---|---|---|---|
| 3,919,265 | 11/1975 | Bugaut et al. | 552/306 |
| 3,929,404 | 12/1975 | Kalopisis et al. | 8/407 |
| 3,973,901 * | 8/1976 | Micchelli et al. | 8/425 |
| 4,023,926 | 5/1977 | Bugaut et al. | 8/407 |
| 4,046,786 | 9/1977 | Kalopissis et al. | 552/302 |
| 4,084,052 | 4/1978 | Bugaut et al. | 544/165 |
| 4,093,806 | 6/1978 | Kalopissis et al. | 544/165 |
| 4,204,059 | 5/1980 | Bugaut et al. | 544/166 |
| 4,213,960 | 7/1980 | Grollier et al. | 424/47 |
| 4,260,749 | 4/1981 | Bugaut et al. | 544/166 |
| 4,402,977 | 9/1983 | Grollier et al. | 424/70.13 |
| 5,030,443 | 7/1991 | Varco et al. | 424/47 |
| 5,160,730 * | 11/1992 | Dubief et al. | 424/59 |
| 5,221,530 * | 6/1993 | Janchitraponvej et al. | 424/70.11 |
| 5,368,850 * | 11/1994 | Cauwet et al. | 424/70.11 |
| 5,422,031 * | 6/1995 | Nomura et al. | 8/435 |
| 5,603,926 * | 2/1997 | Matsumoto et al. | 424/70.15 |
| 5,607,482 * | 3/1997 | Reiff et al. | 8/495 |
| 5,635,461 * | 6/1997 | Onitsuka et al. | 8/406 |
| 5,645,609 * | 7/1997 | Andrean et al. | 8/405 |
| 5,753,215 * | 5/1998 | Mougin et al. | 424/70.11 |

FOREIGN PATENT DOCUMENTS

| | | |
|---|---|---|
| 3 044 754 | 6/1981 | (DE) . |
| 9 413 897 | 2/1996 | (DE) . |
| 100808 * | 2/1984 | (EP) . |
| 0 445 714 | 9/1991 | (EP) . |
| 0 503 507 | 9/1992 | (EP) . |
| 2 189 380 | 1/1974 | (FR) . |
| 2 234 277 | 1/1975 | (FR) . |
| 2 382 232 | 9/1978 | (FR) . |

OTHER PUBLICATIONS

Caplus Abstract JP 63–218,614, Mitsubishi Petrochemical Co., Sep. 1988.*
Caplus Abstract of PL 150,380, Osrodek Badawczo–Rozwojowy Przemyslu Barwnikow, May 1990.*
Venkataraman, The Chemistry of Synthetic Dyes, vol. V, Academic Press, pp. 532–534, 1971 (No Month Available).*

\* cited by examiner

*Primary Examiner*—Caroline D. Liott
(74) *Attorney, Agent, or Firm*—Finnegan, Henderson, Farabow, Garrett & Dunner, L.L.P.

(57) ABSTRACT

The invention discloses a capillary dyeing composition comprising at least one direct dye, characterised in that it further contains a cross-linked polymer with acrylic and/or acrylate units and with acrylamide units. The invention also discloses the use of a cross-linked polymer with acrylic and/or acrylate units and with acrylamide units, in or for the production of a dyeing composition containing at least one direct dye, to improve the tinctorial power of the said composition, particularly after storage at below about 10° C., and particularly at about 4° C. The invention also discloses a method for preserving the tinctorial power, in particular after storage at a temperature below about 10° C., of a dyeing composition containing at least one direct dye, characterised in that an effective amount of the said cross-linked polymer is added to the composition.

32 Claims, No Drawings

DIRECT HAIR DYEING COMPOSITION COMPRISING A CROSS-LINKED POLYMER WITH ACRYLIC AND/OR ACRYLATE UNITS AND WITH ACRYLAMIDE UNITS

The invention relates to a composition for dyeing the hair, comprising at least one direct dye and at least one crosslinked polymer containing acrylic and/or acrylate units and acrylamide units.

It is known to dye hair fibres with direct dye compositions according to a so-called "direct dyeing" process which consists in applying to the fibres dye molecules which have an affinity for the said fibres, in leaving them to stand on the fibres and then in rinsing the fibres. The resulting colorations are temporary or semi-permanent colorations depending on the nature of the interactions between the direct dyes and the hair fibre, and their desorption from the surface and/or from the core of the fibre.

In order to facilitate the application of such dye compositions to the hair, in particular to prevent them from running down the forehead and the face or beyond the point of application initially chosen, when they are applied or during the exposure time required for dyeing, the viscosity of the compositions is conventionally increased using crosslinked polyacrylic acid (thickener). However, dye compositions based on direct dyes and on crosslinked polyacrylic acid no longer prove to be sufficiently satisfactory as regards their dyeing properties after they have been stored for a certain period at a temperature below room temperature, for example below 10° C., and in particular at about 4° C. Thus, it is observed that compositions stored under such conditions give rise to a weaker rise of the direct dye on the hair and thus have an insufficient dyeing power.

The present invention aims to solve the above problem, i.e. to propose a means which makes it possible to preserve the dyeing power of dye compositions containing a direct dye, for compositions liable to be stored at low temperatures, in particular at temperatures below 10° C.

After considerable research conducted in this matter, the Applicant has now discovered that it is possible to preserve the dyeing power of direct dye compositions if an effective amount of a crosslinked polymer containing acrylic and/or acrylate units and acrylamide units is added to these compositions.

Even after relatively prolonged storage at temperatures below 10° C., and in particular close to 4° C., compositions with good dyeing power and whose rise on the hair is very satisfactory are obtained.

This discovery forms the basis of the present invention.

The subject of the present invention is thus a cosmetic composition for dyeing the hair, of the type comprising, in a cosmetically acceptable support which is suitable for dyeing, at least one direct dye, and which is characterized in that it also comprises at least one crosslinked polymer containing acrylic and/or acrylate units and acrylamide units.

The subject of the present invention is also the use of a crosslinked polymer containing acrylic and/or acrylate units and acrylamide units, in, or for the manufacture of, a direct dye composition for the hair, comprising at least one direct dye, in order to improve the conservation of the dyeing power of the said composition, in particular after storage below about 10° C., and especially at about 4° C.

The invention also relates to a process for improving the conservation of the dyeing power, in particular after storage below about 10° C., and especially at about 4° C., of a dye composition for the hair comprising at least one direct dye, this process consisting in introducing an effective amount of at least one crosslinked polymer containing acrylic and/or acrylate units and acrylamide units into the said composition.

Lastly, the invention relates to a process for dyeing the hair using the compositions with improved properties in accordance with the invention.

However, other characteristics, aspects, objects and advantages of the invention will become even more apparent on reading the description and the examples which follow.

According to the invention, the expression acrylic and/or acrylate units is understood to denote units of structure:

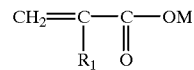

in which, $R_1$ denotes H or $CH_3$, preferably H,

M denotes hydrogen, an ammonium, an alkali metal such as sodium or potassium or a primary or secondary monoamine, and preferably an ammonium.

The term acrylamide units is also understood to denote units of structure:

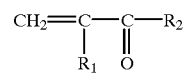

in which, $R_1$ denotes H or $CH_3$, preferably H, $R_2$ denotes an amino, dimethylamino, tert-butylamino or —NH—$CH_2$OH radical, and preferably an amino radical.

Preferably, the polymers used in the context of the present invention are polymers of the type containing acrylate units (M other than H) and containing acrylamide units, crosslinked using a suitable crosslinking agent.

The crosslinked polymer(s) containing acrylic and/or acrylate units and acrylamide units, which can be used in the context of the present invention, are thus, more particularly, ammonium acrylate/acrylamide or sodium acrylate/acrylamide copolymers crosslinked by a compound containing olefinic polyunsaturation, preferably chosen from divinylbenzene, tetraallyloxyethane, methylenebisacrylamide, diallyl ether, polyallylpolyglyceryl ethers or allylic ethers of alcohols from the sugar series, such as erythritol, pentaerythritol, arabitol, mannitol, sorbitol or glucose.

Crosslinked copolymers of this type are described and prepared in French patent FR-2,416,723 and U.S. Pat. Nos. 2,798,053 and 2,923,692.

According to the invention, it is most particularly preferred to use crosslinked copolymers of the ammonium acrylate/acrylamide type, and even more preferably a 95/5 by weight copolymer of this type, in the form of a water-in-oil emulsion consisting of about 32% by weight of the said copolymer, about 20% by weight of $C_{11}$–$C_{13}$ isoparaffin, 2% by weight of sorbitan sesquioleate, 3% by weight of a hydrophilic ethoxylated derivative and 43% by weight of water. Such an emulsion is marketed by the company Hoechst under the name Bozepole C Nouveau.

The crosslinked polymer containing acrylic and/or acrylate units and acrylamide units is generally used in the dye composition according to the invention in active material proportions which can be from about 0.05 to about 5% by weight and preferably from 0.1 to about 3% by weight, relative to the total weight of the composition.

The direct dyes which can be used in the dye composition according to the present invention are direct dyes in the sense defined above, that is to say dyes which can be used in a standard direct dyeing process.

Among those used conventionally, mention may be made of nitrobenzene dyes such as nitrophenylenediamines, nitrodiphenylamines, nitroanilines, nitrophenols or nitrophenol ethers, nitropyridines, anthraquinone, mono- or diazo, triarylmethane, azine, acridine and xanthene dyes or alternatively metalliferous dyes.

The direct dyes more particularly preferred according to the invention are chosen from the following:

i) the nitrobenzene dyes of formula (I) below:

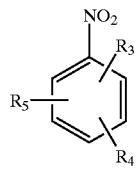

(I)

in which:
- $R_3$ denotes an $NH_2$ radical, an amino radical monosubstituted with an alkyl, monohydroxyalkyl, polyhydroxyalkyl or aminoalkyl radical, or an amino radical disubstituted with identical or different alkyl, mono- or polyhydroxyalkyl or aminoalkyl radicals,
- $R_4$ denotes hydrogen, hydroxyl, alkoxy, mono- or polyhydroxyalkyloxy, or the same meanings denoted above for $R_3$, except for the disubstituted amino radical,
- $R_5$ denotes hydrogen, alkyl, nitro or halogen, ii) the anthraquinone dyes of the formula (II) below:

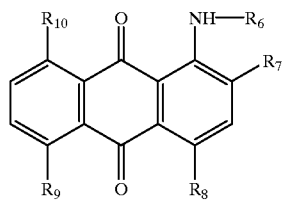

(II)

in which
- $R_6$ denotes hydrogen or a monohydroxyalkyl or polyhydroxyalkyl radical,
- $R_7$ denotes hydrogen or an alkyl or alkoxy radical,
- $R_8$ denotes hydrogen or a hydroxyl, amino, monohydroxyalkylamino or polyhydroxyalkylamino radical
- $R_9$ and $R_{10}$, which may be identical or different, are hydrogen, hydroxyl or amino, iii) the azo dyes of formula (III) below:

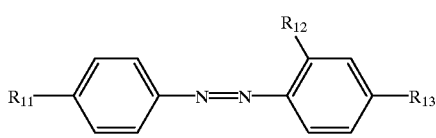

(III)

in which:
- $R_{11}$ denotes a nitro or amino radical or an amino radical mono- or disubstituted with alkyls,
- $R_{12}$ denotes hydrogen or an alkyl radical,
- $R_{13}$ denotes an amino radical or an amino radical mono- or disubstituted with monohydroxyalkyls, it being understood that the alkyl and alkoxy radicals mentioned above in formulae (I), (II), and (III) are $C_1$–$C_4$ and that they can be linear or branched, and the cosmetically acceptable salts of all these compounds.

The term $C_1$–$C_4$ is understood to refer in particular to the methyl, ethyl, n-propyl, isopropyl, n-butyl, sec-butyl and tert-butyl radicals.

The expression cosmetically acceptable salts is understood more particularly to denote the hydrochlorides, hydrobromides and sulphates.

Even more advantageously, according to the present invention, it is preferred to use the following direct dyes:
1-amino-2-nitro-4-N-(β-hydroxyethyl)amino-5-methylbenzene,
1,4,5,8-tetraaminoanthraquinone,
1,4-bis-N-N'-[(β, γ-dihydroxypropyl)amino]-anthraquinone
1,4,4-N-tris(β-hydroxyethyl)-1,4-diamino-2-nitro-benzene,
1-N-(β-hydroxyethyl)amino-2-nitro-4-aminobenzene,
1-hydroxy-3-nitro-4-aminobenzene,
1-hydroxy-3-nitro-4-N-(β-hydroxyethyl)aminobenzene,
1-β-hydroxyethyloxy-3-methylamino-4-nitrobenzene,
1-methylamino-2-nitro-5-β, γ-dihydroxypropyloxybenzene,
1-N-(β-aminoethyl)amino-2-nitro-4-β-hydroxyethyloxybenzene
4-[N-ethyl-N-(β-hydroxyethyl)amino]-1-N-(β-hydroxyethyl)amino-2-nitrobenzene,
1-(4'-aminodiphenylazo)-2-methyl-4-N-bis(β-hydroxyethyl-aminobenzene,
1-methoxy-3-N-(β-aminoethyl)amino-4-nitrobenzene,
1-amino-2-nitro-4-N-(β-hydroxyethyl)aminobenzene,
1-amino-2-nitro-4-N-bis(β-hydroxyethyl)aminobenzene,
1,4-N-bis(β-hydroxyethyl)amino-2-nitrobenzene,
1-amino-2-N-(β-hydroxyethyl)amino-5-nitrobenzene,
1,4-diaminoanthraquinone,
and the cosmetically acceptable salts thereof.

These direct dyes, in salified or base form, are generally present in the dye composition according to the invention in proportions which can range from about 0.001 to about 10% by weight, and preferably from about 0.05 to about 5% by weight, relative to the total weight of the composition.

The cosmetically acceptable medium for the dyeing is an aqueous medium which can contain one or more organic solvents chosen, for example, from ethyl alcohol, isopropyl alcohol, benzyl alcohol and phenylethyl alcohol, or glycols or glycol ethers such as, for example, propylene glycol or its ethers such as, for example, propylene glycol monomethyl ether, butylene glycol, dipropylene glycol, ethylene glycol monomethyl, monoethyl and monobutyl ethers, and diethylene glycol alkyl ethers such as, for example, diethylene glycol monoethyl ether or monobutyl ether, in proportions of approximately between 0.5 and 20% by weight, and preferably approximately between 2 and 10% by weight, relative to the total weight of the composition.

Fatty amides such as mono- and diethanolamides of coconut-derived acids, of lauric acid or of oleic acid, at concentrations of approximately between 0.05 and 10% by weight can also be added to the composition according to the invention.

Surfactants that are well known in the state of the art and of anionic, cationic, nonionic, amphoteric or zwitterionic type or mixtures thereof can also be added to the composition according to the invention, preferably in a proportion of approximately between 0.1 and 50% by weight, and advantageously approximately between 1 and 20% by weight, relative to the total weight of the composition.

The said dye composition can also contain various common adjuvants such as antioxidants, fragrances, sequestering agents, dispersing agents, hair conditioners, preserving agents and opacifiers, as well as any other adjuvant usually used to dye human keratin fibres, and especially the hair.

Needless to say, a person skilled in the art will take care to select the optional complementary compound(s) mentioned above such that the advantageous properties intrinsically associated with the dye composition according to the invention are not, or are not substantially, adversely affected by the addition(s) envisaged.

The dye composition according to the invention can be formulated at acidic, neutral or alkaline pH, it being possible for the pH to vary, for example, from 3 to 12 and preferably from 7 to 11 and even more preferably from 8.5 to 10, and for it be adjusted using basifying agents or acidifying agents that are previously well known. As basifying agents, mention may be made of aqueous ammonia, alkaline carbonates, alkanolamines, for example mono-, di- and triethanolamines and derivatives thereof, sodium hydroxide, potassium hydroxide, and compounds of formula:

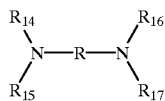

in which R is a propylene residue optionally substituted with a hydroxyl group or a $C_1$–$C_4$ alkyl radical; $R_{14}$, $R_{15}$, $R_{16}$ and $R_{17}$, simultaneously or independently of each other, represent a hydrogen atom or a $C_1$–$C_4$ alkyl or $C_1$–$C_4$ hydroxyalkyl radical.

The acidifying agents are conventionally inorganic or organic acids such as, for example, hydrochloric acid, tartaric acid, citric acid and phosphoric acid.

The composition applied to the hair can be in various forms, such as in the form of a liquid, a cream or a gel or in any other form which is suitable for dyeing the hair. In particular, it can be packaged under pressure in an aerosol can in the presence of a propellant and can form a mousse.

Another subject of the present invention relates to a process for dyeing the hair, by direct dyeing, which consists in applying a dye composition as defined above to wet or dry hair, then in leaving the said composition to act, preferably for 3 to 60 minutes approximately, in rinsing the hair, then optionally in washing it, then in rinsing it again and then in drying it.

It is also possible to leave the composition to act and then dry it.

Concrete examples illustrating the invention will now be given.

EXAMPLE 1

The following dyeing composition was prepared:

| | |
|---|---|
| Direct dye (1)* | 0.1 g |
| Decyl alcohol oxyethylenated with 5.3 mol of ethylene oxide | 2.0 g |
| Lauric acid | 1.0 g |
| Diethylene glycol monobutyl ether | 5.0 g |

-continued

| | |
|---|---|
| Bozepole C Nouveau from Hoechst | 0.9 g AM● |
| 2-Amino-2-methyl-1-propanol | q.s pH 9.5 |
| Demineralized water | q.s.p 100 g |

*dye (1): 1-amino-2-nitro-4-N-(β-hydroxyethyl)amino-5-methylbenzene
AM● denotes active material.

After 24 hours, the viscosity of this composition was measured using a Contrave viscometer at 25° C. The viscosity recorded was 210 cp.

This composition was then applied to locks of natural grey hair containing 90% white hairs and the composition was left to stand on the hair for 30 minutes. The locks were then rinsed with running water and dried.

The locks were dyed in a shade which, quantified in terms of the Munsell value (ASTM standard D 1535-68, which defines the colour: H denoting the shade or Hue, V denoting the intensity or Value, and C denoting the purity or Chromacity), on a Minolta CM 2002 colorimeter, was as follows: in H,V,C: 6.9 R 4.7/3.0.

The control locks (not dyed) had an H,V,C shade: 3.8Y 5.7/1.6.

The composition prepared above was also stored for one month at a temperature of 4° C.

The composition thus stored was then applied to locks of hair of the same quality and according to the same procedure as above.

The shade of the locks dyed using this composition stored at 4° C. was as follows: in H,V,C: 7.9 R 4.7/3.0.

The change in colour between locks dyed using the initial composition and those dyed using the composition stored for one month at a temperature of 4° C., was then quantified using the Nickerson equation which defines the colour variation indices: $I=(C/5)\times 2\Delta H+6\Delta V+3\Delta C$ (this equation being described in the publication:

"Journal of the Optical Society of America", September 1994 Vol. 34, No. 9, pp.550–570.

Thus, the change in Colour $I_b$ (colour variation index between the locks dyed using the composition stored for one month at a temperature of 4° C. and that of the locks dyed using the intial composition) relative to the $I_a$ (colour variation index of the locks dyed using the initial composition and that of the control locks), quantified in %, was 5.7%.

COMPARATIVE EXAMPLE 2

A dye composition similar to that of Example 1 was prepared, with a viscosity equal to that of Example 1, based on polymer of the prior art, by simply replacing the 0.9 g of ammonium acrylate/acrylaminde crosslinked copolymer (Bozepole C Nouveau) by 0.57 g of Carbopol 980 from the company Goodrich (crosslinked polyacrylic acid of the prior art, MW 4,000,000).

Locks of natural hair containing 90% white hairs were dyed using the intital coposition (i.e. before storage) and according to a procedure identical to that of Example 1, in a shade, expressed in terms of H,V,C, equal to: 8.1 R 4.9/2.9. Locks of natural hair containing 90% white hairs were dyed using the same composition but stored for one month at 4° C. The shade obtained was:

H,V,C: 8.7 R 4.8/2.8.

The ratio $I_b/I_a$ applied to this example, and quantified in %, was 8.5%.

Conclusion:

After storage for one month at 4° C., the dye composition of Example 1 comprising a crosslinked polymer in accordance with the present invention has a dyeing power which is considerably superior to that of the dye composition of Example 2 comprising a crosslinked polymer of the prior art, since the degradation, which is expressed by the ratio $I_b/I_a$ quantified in %, is only 5.7% in the case of Example 1 whereas it is 8.5% in the case of Example 2.

EXAMPLE 3

The following dyeing composition was prepared:

| | |
|---|---|
| Direct dye (2)* | 0.1 g |
| Decyl alcohol oxyethylenated with 5.3 mol of ethylene oxide | 2.0 g |
| Lauric acid | 1.0 g |
| Diethylene glycol monobutyl ether | 5.0 g |
| Bozepole C Nouveau from Hoechst | 0.57 g AM● |
| 2-Amino-2-methyl-1-propanol | q.s pH 9.5 |
| Demineralized water | q.s.p 100 g |

*dye (2): 1,4,5,8-tetraaminoanthraquinone (a 30% dispersion on lignosulphate).

After 24 hours, the viscosity of this composition was measured on a Contrave viscometer at 25° C. The viscosity recorded was 190 cp.

This composition was then applied to locks of permanent-waved grey hair containing 90% white hairs and was left to stand on the hair for 30 minutes. The locks were then rinsed with running water and dried.

The locks were dyed in a shade which, quantified in terms of the Munsell value, was as follows, in H,V,C: 4.4 B 4.0/2.4.

The control locks (not dyed) had an H,V,C shade: 4.4 Y 5.9/1.6.

The abovementioned composition was then stored for one month at a temperature of 4° C.

The composition thus stored was then applied to locks of hair of the same quality and according to the same procedure as above.

The shade of the locks dyed using this composition stored at 4° C. was as follows, in H,V,C: 4.7 B 4.2/2.4.

The ratio $I_b$ (colour variation index between the locks dyed using the composition stored for one month at 4° C. and that of the locks dyed using the initial composition) to $I_a$ (colour variation index between the locks dyed using the initial composition and that of the control locks), quantified in %, was 3.8%.

COMPARATIVE EXAMPLE 4

A dye composition similar to that of Example 3 was prepared, with a viscosity equal to that of Example 3, based on polymer of the prior art, by simply replacing the 0.57 g of ammonium acrylate/acrylaminde crosslinked copolymer (Bozepole C Nouveau) by 0.67 g of Carbopol 2984 from the company Goodrich (crosslinked polyacrylic acid of the prior art, MW 3,000,000).

Locks of permanent-waved hair containing 90% white hairs were dyed using the initial composition (i.e. before storage) and according to a procedure identical to that of Example 3, in a shade, expressed in terms of H,V,C, equal to: 5.4 B 4.1/3.1.

Locks of permanent-waved hair containing 90% white hairs were dyed using the same composition but stored for one month at 4° C. The shade obtained was, in terms of H, V, C, equal to: 1.6 B 4.3/1.9.

The ratio $I_b/I_a$ applied to this example, and quantified in %, was 22.9%.

Conclusion:

After storage for one month at 4° C., the dye composition of Example 3 comprising a crosslinked polymer in accordance with the present invention has a dyeing power which is considerably superior to that of the dye composition of Example 4 comprising a crosslinked polymer of the prior art, since the degradation, which is expressed by the ratio $I_b/I_a$ quantified in %, is only 3.8% in the case of Example 3 whereas it is 22.9% in the case of Example 4.

What is claimed is:

1. A composition for dyeing hair comprising, in a cosmetically acceptable support suitable for dyeing, at least one direct dye and at least one crosslinked polymer containing acrylamide residue units and residue units selected from acrylic and acrylate, wherein said at least one direct dye is chosen from:

at least one nitrobenzene dye of formula (I):

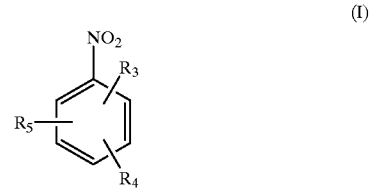

(I)

wherein:

$R_3$ is chosen from an $NH_2$ radical, amino radicals monosubstituted with a radical chosen from alkyl, monohydroxyalkyl, polyhydroxyalkyl, and aminoalkyl radicals, and amino radicals disubstituted with identical or different radicals chosen from alkyl, monohydroxyalkyl, polyhydroxyalkyl, and aminoalkyl radicals, $R_4$ is chosen from hydrogen, hydroxyl radicals, alkoxy radicals, monohydroxyalkyloxy radicals, polyhydroxyalkyloxy radicals, an $NH_2$ radical, and amino radicals monosubstituted with a radical chosen from alkyl, monohydroxyalkyl, polyhydroxyalkyl, and aminoalkyl radicals, and $R_5$ is chosen from hydrogen, alkyl radicals, nitro radicals, and halogen, wherein said alkyl and alkoxy radicals are $C_1$–$C_4$ and are linear or branched;

at least one cosmetically acceptable salt of said nitrobenzene dye of formula (I);

at least one anthraquinone dye of formula (II):

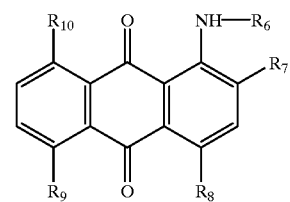

(II)

wherein:

$R_6$ is chosen from hydrogen, monohydroxyalkyl radicals, and polyhydroxyalkyl radicals, $R_7$ is chosen from hydrogen, alkyl radicals, and alkoxy radicals, $R_8$ is chosen from hydrogen, hydroxyl radicals, amino radicals, monohydroxyalkylamino radicals, and polyhydroxyalkylamino radicals, and $R_9$ and $R_{10}$ are independently chosen from hydrogen, hydroxyl radicals, and amino radicals, wherein said alkyl and alkoxy radicals are $C_1$–$C_4$ and are linear or branched;

at least one cosmetically acceptable salt of said anthraquinone dye of formula (II);

at least one azo dye of formula (III):

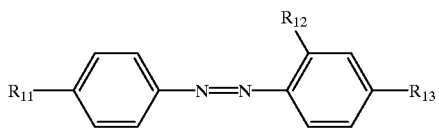

(III)

wherein:

$R_{11}$ is chosen from nitro radicals and amino radicals, wherein said amino radicals may be mono- or disubstituted with identical or different alkyl radicals, $R_{12}$ is chosen from hydrogen and alkyl radicals, and $R_{13}$ is chosen from amino radicals, wherein said amino radicals may be mono- or disubstituted with identical or different monohydroxyalkyl radicals, wherein said alkyl radicals are $C_1$–$C_4$ and are linear or branched; and at least one cosmetically acceptable salt of said azo dye of formula (III).

2. A composition according to claim 1, wherein said at least one crosslinked polymer contains acrylate residue units and acrylamide residue units.

3. A composition according to claim 2, wherein said at least one crosslinked polymer is an ammonium acrylate/acrylamide crosslinked copolymer.

4. A composition according to claim 2, wherein said at least one crosslinked polymer is a sodium acrylate/acrylamide crosslinked copolymer.

5. A composition according to claim 1, wherein said crosslinked polymer was crosslinked utilizing a crosslinking agent containing olefinic polyunsaturation.

6. A composition according to claim 5, wherein said crosslinking agent containing olefinic polyunsaturation is selected from divinylbenzene, tetraallyloxyethane, methylenebisacrylamide, diallyl ether, polyallylpolyglyceryl ethers and allylic ethers of alcohols of a sugar.

7. A composition according to claim 3, wherein said at least one crosslinked polymer is an ammonium acrylate/acrylamide crosslinked copolymer in a proportion of 95:5 by weight of said copolymer.

8. A composition according to claim 7 wherein said copolymer is in the form of a water-in-oil emulsion comprising 32% by weight said copolymer, 20% by weight $C_{11}$–$C_{13}$ isoparaffin, 2% by weight sorbitan sesquioleate, 3% by weight hydrophilic ethoxylated derivative, and 43% by weight water.

9. A composition according to claim 1, wherein said at least one crosslinked polymer is present in an amount ranging from 0.05 to 5% by weight relative to the total weight of said composition.

10. A composition according to claim 9, wherein said at least one crosslinked polymer is present in an amount ranging from 0.1 to 3% by weight relative to the total weight of said composition.

11. A composition according to claim 1, wherein said at least one cosmetically acceptable salt of said azo dye of formula (III) is selected from hydrochlorides, hydrobromides and sulphates.

12. A composition according to claim 1, wherein said cosmetically acceptable salts of said anthraquinone dye of formula (II) is selected from hydrochloride, hydrobromides and sulphates.

13. A composition according to claim 1, wherein said cosmetically acceptable salts of said nitrobenzene dye of formula (I) is selected from hydrochlorides, hydrobromides and sulphates.

14. A composition according to claim 1, wherein said at least one direct dye is present, in salified or base form, in an amount ranging from 0.001 to 10% by weight, relative to the total weight of said composition.

15. A composition according to claim 14, wherein said at least one direct dye is present, in salified or base form, in an amount ranging from 0.05 to 5% by weight, relative to the total weight of said composition.

16. A composition according to claim 1, wherein said cosmetically acceptable support suitable for dyeing is an aqueous support comprising water or water and at least one organic solvent.

17. A composition according to claim 16, wherein said at least one organic solvent is selected from alcohols, glycols and glycol ethers.

18. A composition according to claim 16, wherein said at least one organic solvent is present in an amount ranging from 0.5 to 20% by weight relative to the total weight of said composition.

19. A composition according to claim 18, wherein said at least one organic solvent is present in an amount ranging from 2 to 10% by weight relative to the total weight of said composition.

20. A composition according to claim 1, wherein said composition further comprises at least one adjuvant.

21. A composition according to claim 1, wherein said composition has a pH ranging from 3 to 12.

22. A composition according to claim 21, wherein said composition has a pH ranging from 7 to 11.

23. A composition according to claim 22, wherein said composition has a pH ranging from 8.5 to 10.

24. A composition according to claim 1, wherein said composition is in the form of a liquid, a cream, a gel, or any other form suitable for dyeing hair.

25. A composition according to claim 1, wherein said composition is packaged under pressure in an aerosol can in the presence of at least one propellant.

26. A process of improving the conservation of the dyeing power of a direct dye composition comprising at least one direct dye by including in said composition an effective amount of at least one crosslinked polymer containing acrylamide residue units and residue units selected from acrylic and acrylate, wherein said at least one direct dye and said effective amount of at least one crosslinked polymer are in said direct dye composition in a cosmetically acceptable support suitable for dyeing, and wherein said at least one direct dye is chosen from:

at least one nitrobenzene dye of formula (I):

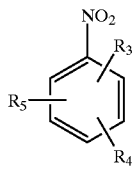

(I)

wherein:

R$_3$ is chosen from an NH$_2$ radical, amino radicals monosubstituted with a radical chosen from alkyl, monohydroxyalkyl, polyhydroxyalkyl, and aminoalkyl radicals, and amino radicals disubstituted with identical or different radicals chosen from alkyl, monohydroxyalkyl, polyhydroxyalkyl and aminoalkyl radicals, R$_4$ is chosen from hydrogen, hydroxyl radicals, alkoxy radicals, monohydroxyalkyloxy radicals, polyhydroxyalkyloxy radicals, an NH$_2$ radical, and amino radicals monosubstituted with a radical chosen from alkyl, monohydroxyalkyl, polyhydroxyalkyl, and aminoalkyl radicals, and R$_5$ is chosen from hydrogen, alkyl radicals, nitro radicals, and halogen, wherein said alkyl and alkoxy radicals are C$_1$–C$_4$ and are linear or branched;

at least one cosmetically acceptable salt of said nitrobenzene dye of formula (I);

at least one anthraquinone dye of formula (III):

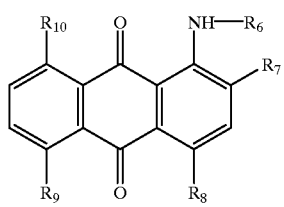

(II)

wherein:

R$_6$ is chosen from hydrogen, monohydroxyalkyl radicals, and polyhydroxyalkyl radicals, R$_7$ is chosen from hydrogen, alkyl radicals, and alkoxy radicals, R$_8$ is chosen from hydrogen, hydroxyl radicals, amino radicals, monohydroxyalkylamino radicals, and polyhydroxyalkylamino radicals, and R$_9$ and R$_{10}$ are independently chosen from hydrogen, hydroxyl radicals, and amino radicals, wherein said alkyl and alkoxy radicals are C$_1$–C$_4$ and are linear or branched;

at least one cosmetically acceptable salt of said anthraquinone dye of formula (II);

at least one azo dye of formula (III):

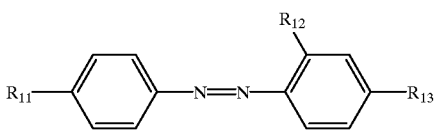

(III)

wherein:

R$_{11}$ is chosen from nitro radicals and amino radicals, wherein said amino radicals may be mono- or disubstituted with identical or different alkyl radicals, R$_{12}$ is chosen from hydrogen and alkyl radicals, and R$_{13}$ is chosen from amino radicals, wherein said amino radicals may be mono- or disubstituted with identical or different monohydroxyalkyl radicals, wherein said alkyl radicals are C$_1$–C$_4$ and are linear or branched; and at least one cosmetically acceptable salt of said azo dye of formula (III).

27. A process according to claim 26 of improving the conservation of the dyeing power of a direct dye composition after storage at low temperatures.

28. A process for dyeing hair by direct dyeing comprising:

applying to said hair when wet or dry an effective amount of a composition comprising, in a cosmetically acceptable support suitable for dyeing, at least one direct dye and at least one crosslinked polymer containing acrylamide residue units and residue units selected from acrylic and acrylate wherein said at least one direct dye is chosen from:

at least one nitrobenzene dye of formula (I):

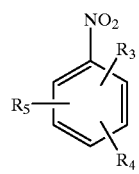

(I)

wherein:

R$_3$ is chosen from an NH$_2$ radical, amino radicals monosubstituted with a radical chosen from alkyl, monohydroxyalkyl, polyhydroxyalkyl, and aminoalkyl radicals, and amino radicals disubstituted with identical or different radicals chosen from alkyl, monohydroxyalkyl, polyhydroxyalkyl, and aminoalkyl radicals, R$_4$ is chosen from hydrogen, hydroxyl radicals, alkoxy radicals, monohydroxyalkyloxy radicals, polyhydroxyalkyloxy radicals, an NH$_2$ radical, and amino radicals monosubstituted with a radical chosen from alkyl, monohydroxyalkyl, polyhydroxyalkyl, and aminoalkyl radicals, and R$_5$ is chosen from hydrogen, alkyl radicals, nitro radicals, and halogen, wherein said alkyl and alkoxy radicals are C$_1$–C$_4$ and are linear or branched;

at least one cosmetically acceptable salt of said nitrobenzene dye of formula (I);

at least one anthraquinone dye of formula (II):

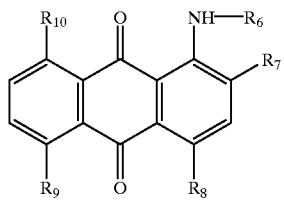

(II)

wherein:

R$_6$ is chosen from hydrogen, monohydroxyalkyl radicals, and polyhydroxyalkyl radicals, R$_7$ is chosen from hydrogen, alkyl radicals, and alkoxy radicals, R$_8$ is chosen from hydrogen, hydroxyl radicals, amino radicals, monohydroxyalkylamino radicals, and polyhydroxyalkylamino radicals, and R$_9$ and R$_{10}$ are independently chosen from hydrogen, hydroxyl radicals, and amino radicals, wherein said alkyl and alkoxy radicals are C$_1$–C$_4$ and are linear or branched;

at least one cosmetically acceptable salt of said anthraquinone dye of formula (II);

at least one azo dye of formula (III):

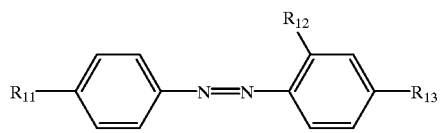

(III)

wherein:

R$_{11}$ is chosen from nitro radicals and amino radicals, wherein said amino radicals may be mono- or disubstituted with identical or different alkyl radicals, R$_{12}$ is chosen from hydrogen and alkyl radicals, and R$_{13}$ is chosen from amino radicals, wherein said amino radicals may be mono- or disubstituted with identical or different monohydroxyalkyl radicals, wherein said alkyl radicals are C$_1$–C$_4$ and are linear or branched; and at least one cosmetically acceptable salt of said azo dye of formula (III).

29. A process according to claim 28, further comprising the steps of, after said applying step, leaving said composition on said hair for a period of time; rinsing said hair; optionally washing and rinsing said hair; and drying said hair.

30. A process according to claim 29, wherein said composition is left on said hair for a period of time ranging from 3 to 60 minutes.

31. A process for dyeing hair by direct dyeing, comprising: applying to said hair when wet an effective amount of a composition comprising, in a cosmetically acceptable support suitable for dyeing, at least one direct dye and at least one crosslinked polymer containing acrylamide residue units and residue units selected from acrylic and acrylate wherein said at least one direct dye is chosen from:

at least one nitrobenzene dye of formula (I):

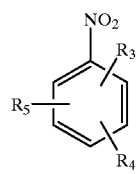

(I)

wherein:

R$_3$ is chosen from an NH$_2$ radical, amino radicals monosubstituted with a radical chosen from alkyl, monohydroxyalkyl, polyhydroxyalkyl, and aminoalkyl radicals, and amino radicals disubstituted with identical or different radicals chosen from alkyl, monohydroxyalkyl, polyhydroxyalkyl and aminoalkyl radicals, R$_4$ is chosen from hydrogen, hydroxyl radicals, alkoxy radicals, monohydroxyalkyloxy radicals, polyhydroxyalkyloxy radicals, an NH$_2$ radical, and amino radicals monosubstituted with a radical chosen from alkyl, monohydroxyalkyl, polyhydroxyalkyl, and aminoalkyl radicals, and R$_5$ is chosen from hydrogen, alkyl radicals, nitro radicals, and halogen, wherein said alkyl and alkoxy radicals are C$_1$–C$_4$ and are linear or branched;

at least one cosmetically acceptable salt of said nitrobenzene dye of formula (I);

at least one anthraquinone dye of formula (II);

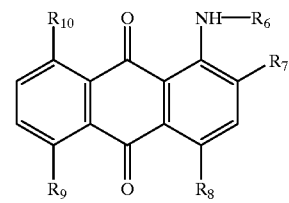

(II)

wherein:

R$_6$ is chosen from hydrogen, monohydroxyalkyl radicals, and polyhydroxyalkyl radicals, R$_7$ is chosen from hydrogen, alkyl radicals, and alkoxy radicals, R$_8$ is chosen from hydrogen, hydroxyl radicals, amino radicals, monohydroxyalkylamino radicals, and polyhydroxyalkylamino radicals, and R$_9$ and R$_{10}$ are independently chosen from hydrogen, hydroxyl radicals, and amino radicals, wherein said alkyl and alkoxy radicals are C$_1$–C$_4$ and are linear or branched;

at least one cosmetically acceptable salt of said anthraquinone dye of formula (II);

at least one azo dye of formula (III):

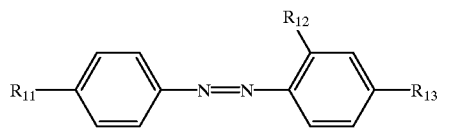

wherein:

$R_{11}$ is chosen from nitro radicals and amino radicals, wherein said amino radicals may be mono- or disubstituted with identical or different alkyl radicals, $R_{12}$ is chosen from hydrogen and alkyl radicals, and $R_{13}$ is chosen from amino radicals, wherein said amino radicals may be mono- or disubstituted with identical or different monohydroxyalkyl radicals, wherein said alkyl radicals are $C_1$–$C_4$ and are linear or branched; and at least one cosmetically acceptable salt of said azo dye of formula (III); and drying said hair.

32. A process according to claim 31, comprising the further step, after said applying step and before said drying step, of waiting a period of time.

* * * * *

UNITED STATES PATENT AND TRADEMARK OFFICE
CERTIFICATE OF CORRECTION

PATENT NO. : 6,187,057
DATED : February 13, 2001
INVENTOR(S) : Mireille MAUBRU

It is certified that error appears in the above-identified patent and that said Letters Patent is hereby corrected as shown below:

Claim 26, col. 11, lines 25-26, delete the line break between "an NH₂" and "radical".

Signed and Sealed this

Fifteenth Day of May, 2001

Attest:

NICHOLAS P. GODICI

*Attesting Officer*     *Acting Director of the United States Patent and Trademark Office*